US008827964B2

(12) United States Patent
Boyd et al.

(10) Patent No.: US 8,827,964 B2
(45) Date of Patent: Sep. 9, 2014

(54) DRUG DELIVERY DEVICE

(75) Inventors: Malcolm Stanley Boyd, Wellesbourne (GB); Robert Frederick Veasey, Lillington Leamington Spa (GB); David Aubrey Plumptre, Droitwich Spa (GB); Stephen Minshull, Holmes Chapel (GB); Christopher James Smith, Holmes Chapel (GB); Patrick Gerard Linnane, Parma (IT)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/202,249

(22) PCT Filed: Mar. 4, 2010

(86) PCT No.: PCT/EP2010/052729
§ 371 (c)(1),
(2), (4) Date: Feb. 13, 2012

(87) PCT Pub. No.: WO2010/100213
PCT Pub. Date: Sep. 10, 2010

(65) Prior Publication Data
US 2012/0130316 A1    May 24, 2012

(30) Foreign Application Priority Data
Mar. 5, 2009   (EP) .................................... 09003182

(51) Int. Cl.
A61M 5/14    (2006.01)
A61B 19/00   (2006.01)
A61M 3/00    (2006.01)
A61M 5/24    (2006.01)
A61M 5/315   (2006.01)

(52) U.S. Cl.
CPC ........... *A61M 5/24* (2013.01); *A61M 2205/584* (2013.01); *A61M 2205/583* (2013.01); *A61M 5/31525* (2013.01)
USPC ........................... 604/254; 604/404; 604/189

(58) Field of Classification Search
CPC ............... A61M 2205/583; A61M 2205/6081; A61M 2205/584; A61M 5/20; A61M 2205/3344; A61J 2205/20; A61B 2019/444; G01K 11/12
USPC ............ 604/97.02–97.03, 318, 404, 254, 189
See application file for complete search history.

(56) References Cited

U.S. PATENT DOCUMENTS 7,214,213 B2     5/2007  Michel et al.
2001/0048891 A1*  12/2001  McGeorge et al. ............. 422/22
(Continued)

FOREIGN PATENT DOCUMENTS

DE   202006007907 U1   7/2006
EP   1923083 A1        5/2008
EP   1923084 A1        5/2008
EP   2201973 A1        6/2010
GB   2402919 A         12/2004
(Continued)

OTHER PUBLICATIONS
Form PCT/IB/326, Notification Concerning Transmittal of International Preliminary Report on Patentability.
(Continued)

*Primary Examiner* — Nicholas Lucchesi
*Assistant Examiner* — Rebecca E Eisenberg
(74) *Attorney, Agent, or Firm* — McDonnell Boehnen Hulbert & Berghoff LLP

(57) ABSTRACT

The present invention relates to a drug delivery comprising a housing (10) adapted to retain a cartridge (16) and a piston rod (26), the piston rod (26) being adapted to drive a piston (28) so as to engage the piston (28) into the cartridge (16) in response to operating an operating button (30), and an indicator means (40) being capable of revealing usage related information of the drug delivery device (5), the indicator means (40) being movable with respect to the housing (10). Furthermore, using indicator means (40) on a drug delivery device (5), wherein the so as to reveal usage related information of the drug delivery device (5), wherein the indicator means (40) being movable with respect to a housing (10) of the drug delivery device (5) is disclosed.

10 Claims, 4 Drawing Sheets

(56) References Cited

U.S. PATENT DOCUMENTS

Figure 1:
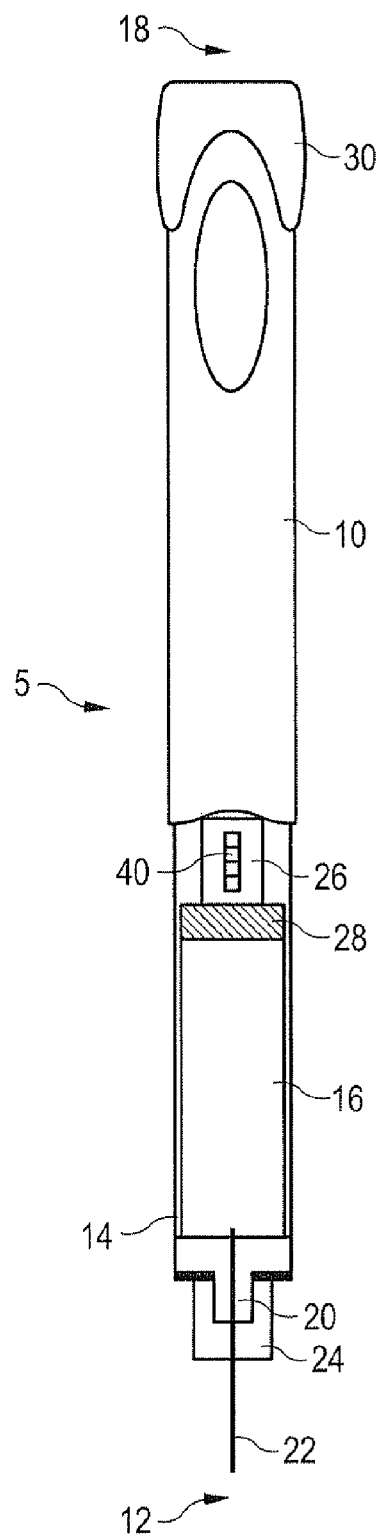

| | | |
|---|---|---|
| 2001/0053894 A1 | 12/2001 | Steenfeldt-Jensen et al. |
| 2005/0131355 A1* | 6/2005 | Kirchhofer et al. ............ 604/187 |
| 2007/0100288 A1* | 5/2007 | Bozeman et al. ............. 604/181 |
| 2008/0269688 A1* | 10/2008 | Colucci et al. ................ 604/189 |
| 2009/0069746 A1* | 3/2009 | Miller et al. .................... 604/67 |
| 2011/0238017 A1* | 9/2011 | Watanabe et al. ............. 604/189 |
| 2012/0107783 A1* | 5/2012 | Julian et al. ................... 434/262 |
| 2012/0310169 A1* | 12/2012 | Sonderegger et al. ........ 604/189 |

FOREIGN PATENT DOCUMENTS

| | | |
|---|---|---|
| WO | 9730742 A1 | 8/1997 |
| WO | 2004020028 A1 | 3/2004 |
| WO | 2007134066 A2 | 11/2007 |
| WO | 2008146021 A1 | 12/2008 |

OTHER PUBLICATIONS 10706644.1 Communication Pursuant to Rule 114(2) EPC dated Sep. 14, 2012.

\* cited by examiner

DRUG DELIVERY DEVICE

CROSS REFERENCE TO RELATED APPLICATIONS

The present application is a 35 U.S.C. 371 National Application of PCT/EP2010/052729 filed Mar. 4, 2010, which claims priority to European Patent Application No. 09003182.4, filed Mar. 5, 2009, the entire contents of which are incorporated entirely herein by reference.

The present invention relates to drug delivery devices. Furthermore, the present invention relates to using a plurality of symbols on a piston rod to represent dosage information during operation of the drug delivery device.

Drug delivery devices are generally known for the administration of a medicinal product, for example insulin, growth hormones or other drugs, in particular medicinal products being suitable for self-administration by a patient, i.e. by a person without formal medical training.

Some drug delivery devices are configured to deliver a plurality of doses. One particular example of such a drug delivery device is described in the document EP 1 923 083 A1 and EP 1 923 084 A1.

There, a drug delivery device is shown where a user may activate the drug delivery device. The drug delivery device includes a drive mechanism suitable for use in pen-type injectors, wherein a number of pre-set doses of medicinal product can be administered. A needle unit can be attached to the drug delivery device for dispensing the medicinal product into a patient's skin. After usage of the drug delivery device, the distal end of the device can be covered by a cap.

Additionally, some drug delivery devices are configured to allow setting of different dose sizes which are to be delivered.

In the document GB 2402919 A, a medical device is shown. A medical device when packaged carries an invisible latent marking, which becomes visible upon exposure to ambient conditions of usage. The marking becomes visible in response to conditions such as light, the atmosphere and/or temperature. The marking may be carried by a permanently attached label or etched into the surface of the device. The device may be a guide for a hypodermic needle as shown, or a cannula, catheter, speculum, spatula, face mask or protective glove. The presence of the visible marking indicates that the device has been used and should be disposed of.

In WO 2008/146021 A1 an auto-injector for a syringe is shown that is suitable for use in the injected delivery of drug to a patient. The auto-injector comprises a housing arranged for receipt of a syringe containing a liquid drug formulation, an actuating mechanism for actuating said syringe to deliver said liquid formulation to a patient and a visual indicator comprising a colour change material that defines a first colour state below a transition temperature and a second colour state above said transition temperature. The visual indicator is arranged to allow the user to differentiate between a 'too cold to use' state (i.e. below the transition temperature) and a 'sufficiently warm to use' state.

It is generally advisable that the user is aware of the previous use of a drug delivery device or is guided through the use of the drug delivery device during a present step of administering a drug.

It is an aim of the present invention to provide for an improved drug delivery device. In particular, a drug delivery device should be provided, which allows for indicating information about prior or actual use of a device to a user.

For this aim, a drug delivery device comprises a housing adapted to retain a cartridge and a piston rod, the piston rod being adapted to drive a piston so as to engage the piston into the cartridge in response to operating an operating button. The device further comprises an indicator means being capable of revealing usage related information of the drug delivery device, the indicator means being movable with respect to the housing.

The invention provides the user with either short or long-term information as to the approximate status of the drug delivery device and their personal dose history as indicated by the indicator means. The invention is of particular benefit to those using a drug delivery device for the first time or being unfamiliar with the required dosing schedule and consequently needing further approximate feedback as to when and how much has been dispensed.

This increases feedback of the drug delivery device usage information to the user. Usually, devices have some degree of user feedback as to the status of the drug delivery device. This feedback is generally the dispensable volume or number of doses left in the device and in the case of many variable devices, also informs the user of the amount of dose he is setting. However, once the dose is dispensed, other than remembering the difference between the scales before and after the dose, or remembering how much was dispensed, the user has little other information to let him know that he has recently taken a dose.

According to the invention, usage related information is provided on components of the drug delivery device which are movable with respect to the housing. When the drug is dispensed from the drug delivery device, at least the piston rod and the piston progressively moves forward towards the distal end of the cartridge in response to operating the operating button.

As the indicator means represent usage information which are related to previous or actual operation of the drug delivery device, the user of the drug delivery device can easily gather this information as the indicator means are no longer hidden by the housing and are moving in the field of vision of the user. This allows the user to quickly gain information regarding the drug delivery device.

In a first embodiment, the indicator means is sensitive to ambient changes.

When dispensing a dose, the user may directly interfere with the indicator means. Alternatively or additionally, the indicator means located on the movable components of the drug delivery device is released so as to be under the influence of the surrounding. Consequently, dispensing a dose would activate the ambient sensitive indicator means, i.e. by changing its state from a first color state to a second color state, for example. Accordingly, the user is informed that a dose has recently been taken so as to receive information regarding the usage of the device.

In one embodiment, the indicator means is pressure sensitive.

In this example, the user would activate the pressure sensitive coating when dispensing a dose by touching the indicator means. Once released, the pressure sensitive indicator means could for example very slowly return to its original state over a period of time. During this time the user is informed that a dose has recently been taken.

Furthermore, this could also be used to ensure that the user holds the device for the correct period of time when dispensing the dose. The state may take a certain period of time to change and once changed, the user would know that the device has been held for the required time. Accordingly, this helps to minimize dose inaccuracies or unintended weeping at the needle.

In one embodiment, the indicator means is temperature sensitive.

If a particular area of the device has been held during dispensing, the user would activate the temperature sensitive coating when dispensing a dose by touching the indicator means. Once released, the indicator means, being provided as a temperature sensitive coating for example, could for example very slowly return to its original state over a period of time. During this time the user is provided with usage related information that a dose has recently been taken.

As already stated above, this could also be used to ensure that the user holds the device for the correct period of time when dispensing the dose. Accordingly, this helps to minimize dose inaccuracies or unintended weeping at the needle.

In one embodiment, the indicator means is light sensitive.

In this example, a light sensitive coating can be applied as a smart material within the drug delivery device, which provides information to the user conveying device status or device history. The indicator means can be located on the movable components of the drug delivery device so as to be under the influence of impinging ambient light. For example, the indicator means can be printed on the drug delivery device using a light sensitive ink or the like. In summary, embodiments of the invention allow the user to ascertain, whether a dose has been taken recently or not, for example.

In one embodiment, the coating is capable of performing a colour change.

Colour change usually attracts the attention and is thus easily recognizable by the user. The time taken for colour change could be used to guide the user as to the amount of time to wait before removing the device from the injection site, for example.

In one embodiment, the indicator means is arranged on the operating button.

In this example, the top of the operating button, which the user presses on to dispense, could be used to remind the user that a dose has been taken. When dispensing a dose, the user would activate the pressure sensitive coating changing its colour or state. Once released, the ambient sensitive coating could very slowly return to its original state over a period of time, for example. During this time the user will know that a dose has recently been taken. The same principal can be achieved by using a heat sensitive material. If a particular area of the device or operating button has been held during dispensing, the area will have changed state or colour, thus indicating to the user that the device has recently been used.

In one embodiment, the indicator means is located underneath an at least partially transparent side wall of the housing.

In this embodiment, the indicator means can be arranged within the housing. The operating means would only be visible, if a dose has been taken. Due to the fact that the operating means is movable, the operating means will become visible by moving underneath the at least partially transparent side wall. For example, the at least partially transparent side wall can be a window or a transparent part close to the cartridge holder. As such, the operating means can be attached to any part used in connection with a dispense mechanism, for example.

In one embodiment, the indicator means is located on the piston rod.

Providing the indicator means on the piston rod does not add any additional components to the drug delivery device and is therefore a cost efficient and viable way of obtaining and displaying usage related information. As virtually all pen-type drug delivery devices include a piston rod of some specific form, the inventive concept can be applied to any drug delivery device irrespective of the precise form of the piston rod.

In one embodiment, the indicator means is located on a part of the operating button being inwardly extending within the housing.

This embodiment would allow the operating means to be one colour when it is exposed to light and another colour when it is hidden by the housing. The time taken for the colour change could be used to guide the user as to the amount of time to wait before removing the device from the injection site. This example is in particular useful when providing a window underneath the part of the operating button that is inwardly extending within the housing. As the operating button is moving before and after injection of a dose, the indicator means guides the user through the medication, for example.

In one embodiment, the indicator means comprises a plurality of symbols.

In this example, several ambient sensitive coatings can be applied so as to form the plurality of symbols. Consequently, different symbols can guide the user through the medication, for example.

In one embodiment, the plurality of symbols is arranged as a progressively advancing scale.

Light sensitive ink or material used for the indicator means on the piston rod or on one side of the piston rod could convey device history or dose timing to the user, for example.

In one embodiment, the colour change is effected comparable to the duration of administering a drug or comparable to the time interval between successive steps of administering a drug.

This embodiment could be a used as dose reminder as well, where the exposed section of the component would change from one colour to another over the period between two subsequent doses. Once fully changed it would be time for the next dose. This particular embodiment is for example suited to fixed dose or fixed schedule devices to indicate whether a dose has recently been dispensed.

In one embodiment, the colour change is effected as a gradual gradient dependant on the duration of the exposure to light.

If the colour change is a gradual gradient dependant on the duration of the exposure to light, as the piston rod advances out of the housing, incremental amounts of the light sensitive material will be gradually exposed over time. As more of the component is exposed it will produce a gradual colour change corresponding to the size and/or approximate time since last dose. This could be compared to a colour scale within the packaging to convey to the user the approximate dose history.

For the above mentioned aim, an indicator means on a drug delivery device is used, wherein the indicator means reveal usage related information of the drug delivery device, and wherein the indicator means being movable with respect to a housing of the drug delivery device.

Using indicator means increases feedback of drug delivery device information to the user. Individually or combined, indicator means allows the user to ascertain the approximate dose timeline, or simply inform the user whether a dose has been taken recently or not. This can include a pressure or temperature sensitive operating button surface combined with a light sensitive piston rod that can gradually change colour depending on the exposed time duration.

Furthermore, this can offer the user immediate short-term feedback as to whether a dose had been taken and, in addition to that, a longer-term feedback about the dose history, if compared with a colour gradient and timescale. In the case of variable doses, the size and gradient of the colour changes could also approximate the recent dose volumes as well as the approximate timings.

Other features will become apparent from the following detailed description when considered in conjunction with the accompanying drawings.

Figure 2A:
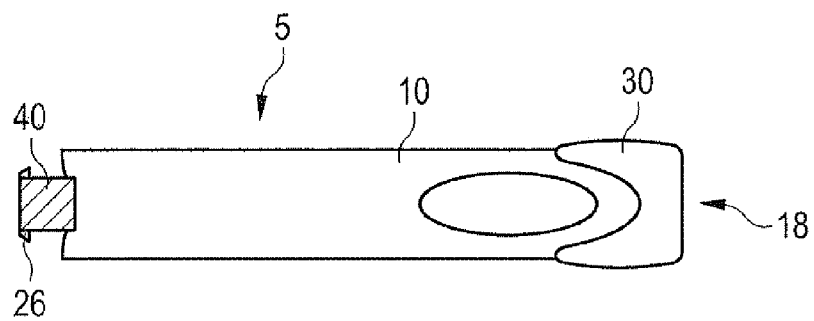
Figure 2B:
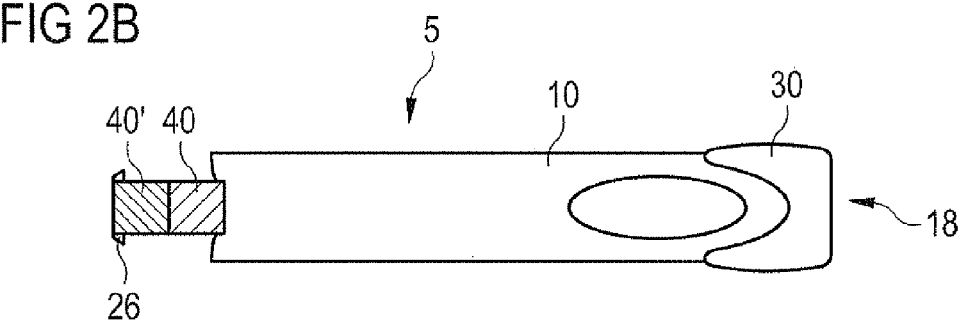
Figure 2C:
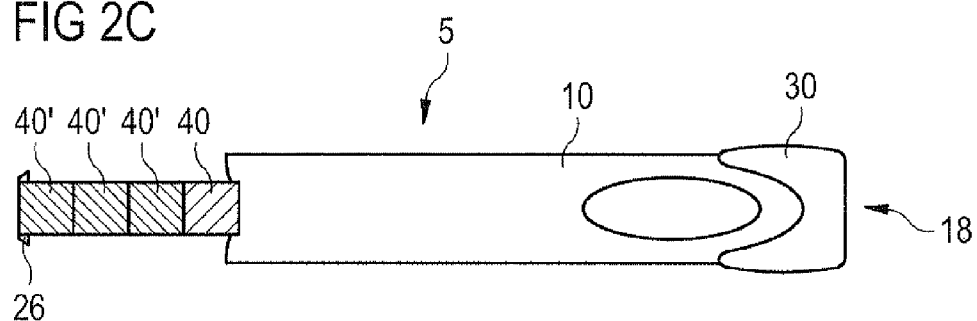
Figure 3A:
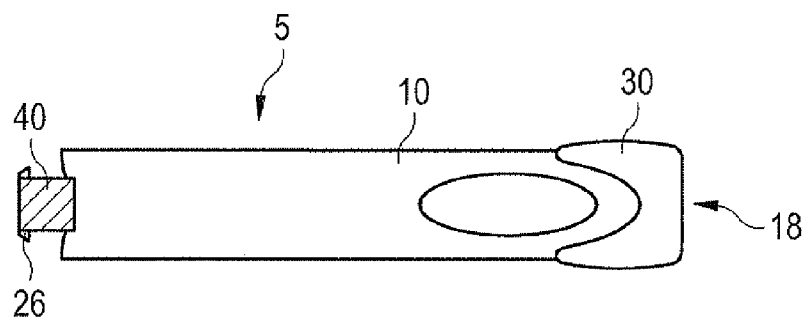
Figure 3B:
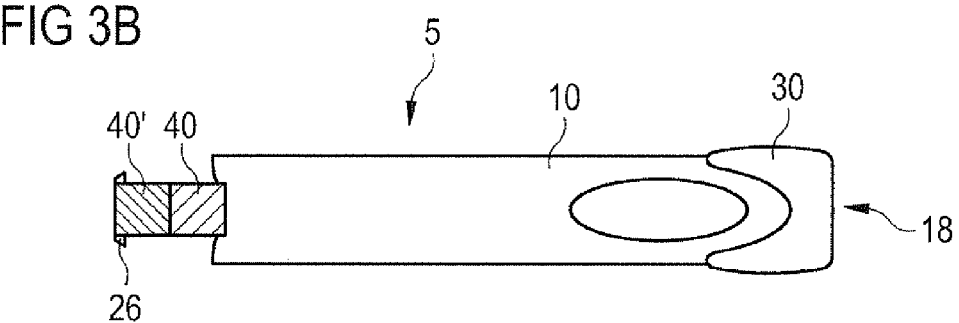
Figure 3C:
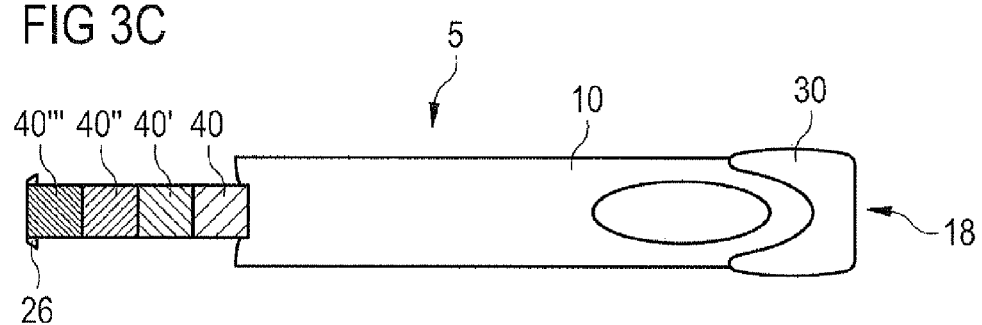
Figure 4:
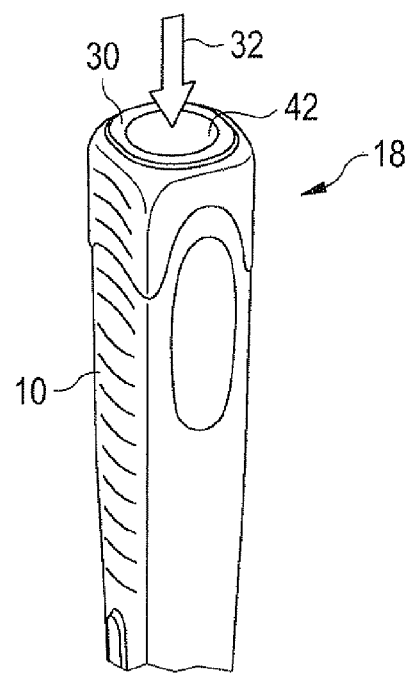
Figure 5:
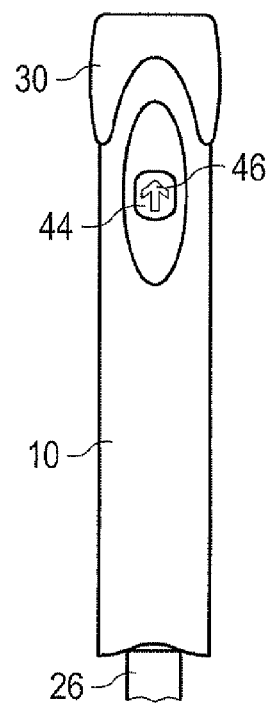
Figure 6:
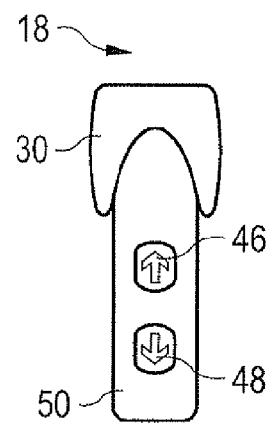

In the drawings:

FIG. 1 schematically shows a simplified side view of a drug delivery device according to an embodiment;

FIGS. 2A to 2C schematically show a simplified side view of a part of a drug delivery device according to an embodiment;

FIGS. 3A to 3C schematically show a simplified side view of a part of a drug delivery device according to an embodiment;

FIG. 4 schematically shows a simplified side view of a part of a drug delivery device according to an embodiment;

FIG. 5 schematically shows a simplified side view of a part of a drug delivery device according to an embodiment; and FIG. 6 schematically shows a simplified side view of a part of a drug delivery device according to an embodiment.

In FIG. 1 an embodiment of a drug delivery device 5 is shown, which is an injector for a liquid medication. It should be noted that the description of the drug delivery device 5 as shown in FIG. 1 is merely illustrative.

The drug delivery device 5 may be configured to deliver a plurality of fixed or user-settable doses of a drug. The drug delivery device 5 may be a pen-type device. The drug delivery device 5 comprises a housing 10, which can be formed from a single or from multiple pieces.

In the embodiment shown in FIG. 1, the housing 10 is attached to a cartridge holder 14, wherein a cartridge 16 containing a medical product or drug can be located. The cartridge holder 14 may be secured against movement with respect to the housing 10. It is also conceivable that cartridge holder 14 and housing 10 are fabricated as a single piece.

A needle unit 24 is located at the distal end 12 of the drug delivery device 5 facing a patient's skin during medication. The needle unit 24 includes a needle 22. Through the needle 22 of the needle unit 24 the medical product can be injected into a patient. The needle unit 24 can be secured to a needle holder 20 by a threaded engagement. The needle holder 20 forms a part of the cartridge holder 14, for example.

Delivery of the medical product can be performed by means of a piston rod 26, which can be moved into the distal direction towards the distal end 12 with respect to the cartridge 16. A piston 28 is retained in the cartridge 16 and seals the cartridge on the side facing the proximal end 30. The piston 28 can be moved in the distal direction 12 with respect to the cartridge by the piston rod 24. The cartridge holder 14 is fabricated from a transparent, partially transparent or translucent material, so as to allow a user to view the position of the piston 28 within the cartridge 16.

The piston rod 26 can be expediently connected to a drive mechanism (not explicitly shown), e.g. a mechanical or electrical drive mechanism, and to a dose setting mechanism (not explicitly shown). Drive mechanism and dose setting mechanism are configured to set a dose of the medical product and to move the piston 28 in the distal direction such that the set dose is dispensed from the cartridge 16 when a operating button 30 of the drug delivery device 5 is pressed.

Piston rod 26 may be linearly movable. Accordingly, the piston rod 26 may translate with respect to the housing 10, when driven in the distal direction. It is, however, also conceivable that piston rod 26 is engaged in a threaded manner with a lead screw nut (not shown in FIG. 1), so as to allow a rotationally movable piston rod 26. During operation of the device, the lead screw nut is secured against rotational movement with respect to the housing 10 by a lock nut which may engage into the lead screw nut. In general, embodiments of the invention are not restricted to a specific configuration of the piston rod, drive mechanism or dose setting mechanism.

As shown in FIG. 1, the piston rod 26 includes an indicator means 40. In case piston rod 26 is fabricated having a square or rectangular cross section, the indicator means 40 can be located on one or more sides of the piston rod 26. However, other forms of the piston rod 26 are conceivable as well, for example a round or oval cross section any other suitable configuration which is known to a person skilled in the art. Indicator means 40 attached to the piston rod 26 can be viewed by a user through the transparent side walls of cartridge holder 14.

According to the embodiment depicted in FIG. 1, indicator means 40 on the piston rod 26 can be provided as a light sensitive ink being printed on the piston rod 26. The light sensitive ink of indicator means 40 provides a colour change in a time interval which is comparable to the duration of administering a drug. It is however also conceivable that the time interval is comparable to the time interval between successive steps of administering a drug.

Making now reference to FIG. 2A, the proximal end 18 of the drug delivery device 5 and the piston rod 26 are shown in more detail. In the embodiment shown in FIG. 2A, the piston rod 26 is constructed as a linearly movable piston rod. On the piston rod 26, a plurality of indicator means 40 are located so as to provide a consecutive array of indicator means. As mentioned above, the cartridge holder 14 includes an at least partially transparent side wall which renders the indicator means 40 of the piston rod 26 at least partially readable.

During operation, the piston 28 and the piston rod 26 progressively advance towards the distal end 12 of the cartridge 16. When the drug contained in the cartridge 16 is dispensed from the drug delivery device 5, the piston 28 advances towards the distal end 12 of the cartridge 16. A first one of the plurality of indicator means 40 on the piston rod 26 is subjected to ambient light impinging through the transparent side wall of the housing 10. In response to the impinging light indicator means 40 is performing a colour change. According to this embodiment a dose reminder can be formed by indicator means 40, where the exposed section of piston rod 26 changes from one colour to another over the period between two successive doses. Once the colour has fully changed, this information can be used to determine that another dose should be applied.

This is further outlined by making reference to FIG. 2B, which shows drug delivery device 5 of FIG. 2A after the second dose has been applied. The indicator means 40' represents the indicator means 40 of the previous application and exhibits a full colour change, as indicated by the dark colour in FIG. 2B. When the drug contained in the cartridge 16 is dispensed from the drug delivery device 5 for the second time, piston rod 26 again advances towards the distal end 12 of the cartridge 16.

A second one of the plurality of indicator means 40 on the piston rod 26 is now subjected to ambient light impinging through the transparent side wall of the housing 10. During the first dispensing step of FIG. 2A, this indicator means 40 is hidden within housing 10 and therefore in the first colour state before the piston rod 26 advances towards the distal end 12 of the cartridge 16. As stated above, indicator means 40 is now performing a colour change in response to the impinging light. The present colour is indicated by the bright colour in FIG. 2B.

Making now reference to FIG. 2C, drug delivery device 5 of FIG. 2B is shown after two more doses have been applied. The indicator means 40' represent the indicator means 40 of the previous applications and exhibit a full colour change, as indicated by the dark colour in FIG. 2C. When the drug contained in the cartridge 16 is dispensed from the drug delivery device 5 once more, the piston 28 again advances towards the distal end 12 of the cartridge 16.

A further one of the plurality of indicator means 40 on the piston rod 26 is now subjected to ambient light impinging through the transparent side wall of the housing 10. The indicator means 40 is now performing a colour change in response to the impinging light. The present colour is indicated by the bright colour in FIG. 2C.

With respect to FIGS. 3A to 3C, a further embodiment of the drug delivery device 5 is shown. Similar to the embodiment of FIGS. 2A to 2C, dispensing a drug in a first, second and fourth step are respectively shown. According to the embodiment depicted in FIGS. 3A to 3C the piston 28 is advanced to some extend into the cartridge 16. Again, the transparent cartridge holder 14 is capable of retaining the piston rod 26 visible during engagement in the cartridge 16.

In this embodiment, the colour change of indicator means 40 is effected as a gradual gradient which depends on duration of an exposure to ambient light.

As shown in FIG. 3A, a first one of the plurality of indicator means 40 on the piston rod 26 is now subjected to ambient light impinging through the transparent side wall of the housing 10. The indicator means 40 is performing a colour change in response to the impinging light.

Making now reference to FIG. 3B, a second one of the indicator means 40 advances out of housing 10. During the first dispensing step of FIG. 3A, this indicator means 40 is hidden within housing 10 and therefore in the first colour state before the piston rod 26 advances towards the distal end 12 of the cartridge 16. The first indicator means 40 has performed a colour change in response to the impinging light and is now indicated by a darker colour in FIG. 3B with reference numeral 40'.

Making now reference to FIG. 3C, drug delivery device 5 of FIG. 3B is shown after two more doses have been applied. A further one of the plurality of indicator means 40 on the piston rod 26 is now subjected to ambient light impinging through the transparent side wall of the housing 10. The indicator means 40 is now performing a colour change in response to the impinging light. The present colour is indicated by the bright colour in FIG. 2C. The indicator means 40''' represent the indicator means 40 of the first application as shown in FIG. 3A. Correspondingly, the indicator means 40'' represent the indicator means 40 of the second application in FIG. 3B. Indicator means 40' represent the indicator means 40 of the third application.

In summary, as the piston rod 26 advances out of the housing 10, incremental amounts on indicator means 40 are gradually exposed over time. As more of the piston rod 26 is exposed to ambient light, indicator means 40 show a gradual colour change which is corresponding to the size and/or approximate time since the last dose.

Making now reference to FIG. 4, the part of the drug delivery device towards the proximal end 18 is shown in more detail.

In the embodiment of FIG. 4, the operating button 30 is covered by a pressure sensitive coating 42 as indicator means 40. When dispensing a dose by touching the indicator means 40, the pressure sensitive coating 42 can change its colour due to the pressure exerted. Once released, the pressure sensitive indicator means could for example very slowly return to its original colour over a period of time. During this time the user is informed that a dose has recently been taken.

In this embodiment, the indicator means 40 can also be temperature sensitive. If a particular area of the device 5 has been held during dispensing, the user would activate the temperature sensitive coating when dispensing a dose by touching the indicator means 40. This could also be used to ensure that the user holds the device 5 for the correct period of time during dispensing the dose. Accordingly, this helps to minimize dose inaccuracies or unintended weeping at the needle.

In summary, arranging the indicator means 40 on the operating button 30, the top of the operating button 30, which the user presses on to dispense, could be used to remind the user that a dose has been taken.

Making now reference to FIG. 4, the part of the drug delivery device 5 towards the proximal end 18 is shown in more detail.

In this embodiment, the indicator means is located on a part of the operating button 30 being inwardly extending within the housing 10. In order to be visible for the user, a window aperture 44 is provided on a side wall of housing 10. This embodiment allows the operating means 40 to be one colour when it is exposed to light through window aperture 44 and another colour when it is hidden by the housing 10. The time taken for colour change could be used to guide the user as to the amount of time to wait before removing the device from the injection site.

This embodiment is in particular useful when providing at least two symbols as indicator means 40. As shown in FIG. 5, the first symbol 46 and second symbol 48 can be located on an inwardly extending part 50 of the operating button 30. Indicator means 40 can be formed using a light sensitive ink in order to print the first symbol 46 and the second symbol 48 as arrows on the operating button. The operating button 30 is moved by the user before and during injection of a dose. Therefore, the first symbol 46 and the second symbol 48 of the indicator means 40 are located at different positions before and after injection of a dose. The respective symbol which is exposed to light impinging through the window aperture 44 shows a colour change and provides the user with information about the device 5. For example, the time taken for the colour change could be used to guide the user as to the amount of time to wait before removing the device from the injection site.

Other implementations are within the scope of the following claims. Elements of different implementations may be combined to form implementations not specifically described herein.

REFERENCE NUMERALS

Drug delivery device 5
Housing 10
Distal end 12
Cartridge holder 14
Cartridge 16
Proximal end 18
Needle holder 20
Needle 22
Needle unit 24
Piston rod 26
Piston 28
Operating button 30
Direction 32
Indicator means 40, 40', 40'', 40'''
Coating 42
Window aperture 44
First symbol 46
Second symbol 48
Inwardly extending part 50

The invention claimed is:

1. A drug delivery device comprising:
a housing adapted to retain a cartridge and a piston rod, the piston rod being adapted to drive a piston so as to engage the piston into the cartridge in response to operating an operating button, and
an indicator revealing usage history information of the drug delivery device,
the indicator being movable with respect to the housing,
wherein the indicator is located underneath an at least partially transparent side wall of the housing
wherein the indicator is sensitive to ambient changes;
wherein the indicator is capable of providing a colour change; and
wherein the colour change is effected comparable to the duration of administering a drug or comparable to the time interval between two successive steps of administering a drug.

2. The drug delivery device according to claim 1, wherein the indicator is pressure sensitive.

3. The drug delivery device according to claim 1, wherein the indicator is temperature sensitive.

4. The drug delivery device according to claim 1, wherein the indicator is light sensitive.

5. The drug delivery device according to claim 1, wherein the indicator is located on the piston rod.

6. The drug delivery device according to claim 1, wherein the indicator is located on a part of the operating button being inwardly extending within the housing.

7. The drug delivery device according to claim 1, wherein the indicator comprises a plurality of symbols.

8. The drug delivery device according to claim 1, wherein a plurality of the indicator is arranged as a progressively advancing scale.

9. The drug delivery device according to claim 1, wherein the colour change is effected as a gradual gradient dependent on the duration of the exposure to light.

10. Using an indicator on a drug delivery device, wherein the indicator reveals usage related information of the drug delivery device, wherein the indicator is movable with respect to a housing of the drug delivery device, and wherein the indicator is located underneath an at least partially transparent side wall of the housing, and
wherein the indicator is sensitive to ambient changes;
wherein the indicator is capable of providing a colour change; and
wherein the colour change is effected comparable to the duration of administering a drug or comparable to the time interval between two successive steps of administering a drug.

* * * * *